United States Patent
Bertl et al.

(10) Patent No.: US 7,320,398 B2
(45) Date of Patent: Jan. 22, 2008

(54) DEVICE FOR STORING AND DISPENSING A FREE-FLOWING SUBSTANCE AND METHOD OF MAKING AND USING THE DEVICE

(75) Inventors: Mathias Bertl, Wildsteig (DE); Marc Peuker, Schondorf (DE); Gabriele Hager, Augsburg (DE)

(73) Assignee: 3M Espe AG, Seefeld (DE)

( * ) Notice: Subject to any disclaimer, the term of this patent is extended or adjusted under 35 U.S.C. 154(b) by 618 days.

(21) Appl. No.: 10/220,606

(22) PCT Filed: Feb. 28, 2001

(86) PCT No.: PCT/EP01/02242

§ 371 (c)(1),
(2), (4) Date: Sep. 3, 2002

(87) PCT Pub. No.: WO01/64544

PCT Pub. Date: Sep. 7, 2001

(65) Prior Publication Data

US 2003/0038040 A1    Feb. 27, 2003

(30) Foreign Application Priority Data

Mar. 1, 2000    (DE) .............................. 100 09 627

(51) Int. Cl.
*B65D 69/00*    (2006.01)
*A61B 19/02*    (2006.01)

(52) U.S. Cl. ................. 206/229; 206/15.3; 206/63.5; 206/209

(58) Field of Classification Search ................. 206/209, 206/209.1, 63.5, 210, 219, 15.3, 361, 229
See application file for complete search history.

(56) References Cited

U.S. PATENT DOCUMENTS

| | | | | |
|---|---|---|---|---|
| 3,713,779 | A * | 1/1973 | Sirago et al. | 206/219 |
| 3,835,834 | A | 9/1974 | Brown et al. | |
| 4,008,803 | A * | 2/1977 | Smith | 206/220 |
| 4,081,077 | A * | 3/1978 | Franck | 206/219 |
| 5,240,415 | A | 8/1993 | Haynie | |
| 5,660,273 | A | 8/1997 | Discko, Jr. | |
| 5,954,996 | A * | 9/1999 | Discko, Jr. | 252/79.1 |
| 6,105,761 | A | 8/2000 | Peuker et al. | |
| 6,116,414 | A * | 9/2000 | Discko, Jr. | 206/229 |
| 6,957,909 | B1 * | 10/2005 | Dingeldein et al. | 220/222 |

FOREIGN PATENT DOCUMENTS

| | | |
|---|---|---|
| DE | 2 157 492 | 11/1971 |
| DE | 3702157 | 6/1988 |
| EP | 0 895 943 | 2/1999 |
| WO | WO/96/03326 | 8/1997 |

* cited by examiner

*Primary Examiner*—Bryon P Gehman
(74) *Attorney, Agent, or Firm*—Crowell & Moring LLP

(57) ABSTRACT

A device can be especially designed for storing and dispensing dental materials. The device comprises a container comprising a first and a second film which form at least one first chamber for receiving a first substance and a recess that is separated from the chamber and serves to remove the first substance. The separation area between the recess and the first chamber is provided with a passage area that can be opened in a selective manner. The first chamber contains at least one additional container.

24 Claims, 4 Drawing Sheets

DEVICE FOR STORING AND DISPENSING A FREE-FLOWING SUBSTANCE AND METHOD OF MAKING AND USING THE DEVICE

BACKGROUND AND SUMMARY OF THE INVENTION

The invention relates to a device, in particular for storing and dispensing dental materials, comprising a container with a first foil and a second foil which form at least one first chamber for receiving a first substance. The device also comprises a pouch which is separate from the chamber and which is used for removing the first substance, the separation between the pouch and the first chamber having a passage area that can be selectively opened, and the first chamber containing at least one further receptacle.

In the dental field in particular, it is often necessary to perform a large number of manual operations in succession and in a coordinated manner.

To fill a cavity of a tooth, for example with a plastic filling, a primer usually has to be applied or blown onto the hard dental substance first, followed by a bonding agent, then exposed to light, if appropriate, before the actual filling can be applied.

While the adhesive substances of primer and bonding agent are usually packaged in bottles in liquid form, the filling material is present as a highly viscous material in screw-cap tubes or is pressed out from what are known as computes.

The dentist applying a filling thus first has to take the primer and bonding agent in the form of a liquid from one package and then remove the filling material in the form of a highly viscous compound from a different package.

The time spent in doing this is not inconsiderable. In addition, the primer and bonding agent from one manufacturer are often not adapted to the chemical composition of the filling material from another manufacturer, which can result in reduced adhesion values on the tooth. Nor can operating errors be ruled out when opening, dispensing and using the substances from the different packages in sequence.

Small quantities of liquid can be stored and applied, for example, using receptacles in the form of blister packs. For example, two recesses separated from one another are provided in the thermoformed part of the package closed off by a removable foil. The first recess can contain a small amount of liquid, and a brush can be placed in the other recess.

WO-96/03326, for example, describes a disposable receptacle which has cavities for storing a medicament and an applicator. Both cavities are protected from contamination by means of a peelable cover foil. In one embodiment, by pressing on the cavity containing the medicament, said medicament is transferred into the cavity containing the applicator in order to wet the applicator. It is explained that this is possible only when the cover foil in the transition area between the two cavities is not bonded to the receptacle. Such a package is not suitable for storing corrosive liquids.

U.S. Pat. No. 3,835,834 discloses a treatment kit which has two cavities in a main body, the cavities containing a care substance on the one hand and a swab on the other. The main body containing the care substance and the swab is protected from contamination by means of a sealing foil.

EP 0 895 943 A discloses a device for storing and dispensing a free-flowing substance, with a container made up of two foils which are connected to one another to form a chamber for receiving the substance and a pouch which is separate from the chamber and used for removing the substance, the separation between the chamber and the pouch having a passage area that can be selectively opened.

Conventionally used peelable sealing foils are not permanently resistant to aggressive media such as strong acids and dipolar aprotic solvents such as acetone. Reaction of these media with the foil constituents can result in delamination of individual foil layers. The storage stability of the filled material and its safe application are thus no longer guaranteed.

It is therefore an object of the present invention to make available a device which avoids these disadvantages.

A further object can be regarded as that of making available a device with which it is possible to store different substance classes inside one package and to dispense them, in particular as a mixture.

There is in particular a need for a device with which it is possible to store individual components of an adhesively acting mixture separately and safely in one package and be able to mix them therein.

This object is achieved by a device and by a method for using the device, as described in the claims.

The words "comprise" or "include" within the meaning of the invention precede a nonexhaustive list of features. The word "one" is to be interpreted as an indefinite quantity with the meaning of "at least one".

The invention has the following advantages:

The presence of a separate receptacle for receiving a substance ensures that in the storage state the substance does not come directly into contact either with the passage area that can be selectively opened or with the foils forming the chamber.

In this way, damage to the device, in particular, the foils forming the device, is made difficult. This permits a longer storage life of the device containing the substance.

In this connection, it has proven advantageous to produce the receptacle using materials which greatly impair or prevent the diffusion of volatile substances.

Depending on the material for the receptacle, aggressive substances can in this way also be stored and handled without problems, without having to forego the advantageous properties of the foils normally used to form the container.

The term aggressive substances includes both corrosive substances (for example acid and basic substances) and tacky substances, and also solvents with the property of attacking plastics.

By means of the device according to the invention, it is also possible, in particular, to safely store substances which are sensitive to radiation. After the foil forming the container, external radiation now has to pass an additional barrier before it can impinge on the substance. Radiation here is to be understood as any form of naturally occurring or artificially generated radiation. This includes, on the one hand, electromagnetic radiation particularly in the range of 380 to 520 nm and, on the other hand, corpuscular radiation, in particular beta radiation.

The device according to the invention also permits unproblematic opening of the chamber by releasing the desired breaking point. The substance which can be present in the chamber can then be transferred into the pouch for removal. At the same time, the device according to the invention can act as a dosing unit for dispensing and applying amounts of substance predetermined by the volume of the chamber.

The device is thus distinguished, in particular, by the fact that, by exerting pressure, a first substance located in a receptacle can be transferred at least partially into a chamber and can be transferred from there into a kind of receiving dish via a passage area that can be selectively opened. Depending on the embodiment, the first substance can be mixed with a second substance before being dispensed or before being transferred into the receiving dish.

The receptacle located in the chamber is preferably arranged or placed in the chamber loosely, in particular, not securely bonded.

If appropriate, the device has a plurality of chambers suitable for receiving substances, which chambers can be connected to one another via passage areas that can be selectively opened.

If appropriate, the device also has a peelable outer layer area. This makes it easy to at least partially remove part of the foil. In this way, at least one chamber containing one or more substances which may be present in separate containers is made visible.

The use of differently configured foils for the outer layer area, on the one hand, and for the foils forming the chamber, on the other hand, permits safe storage of the substances before the device is put to use.

In addition, the substances which are to be mixed are better protected in the storage state from external influences such as incident light or undesired pressure.

If one of the foils forming the chamber is transparent, it is possible, after removing the peelable outer layer area, to visually monitor the mixing procedure and/or the emptying of the chamber. In this way, it is possible to achieve a more homogeneous mixing result and more complete emptying of the chamber into the pouch.

Depending on the substance to be applied, the inner layer of the foil coming into contact with the substance to be applied can be adapted to the properties of the substance. This allows the device to be used to store a large number of substances which differ in terms of their reactivity, without having to substantially modify the method for producing the device.

This embodiment thus allows, for example, dental material to be stored and dispensed safely and in a manner protected from contamination.

If appropriate, a further chamber which cannot be connected to the first chamber or, if appropriate, second chamber via a passage area that can be selectively opened is provided on a second portion. This further chamber is preferably closed off with a separately peelable cover foil which can, if appropriate, be closed again. This permits the storage of at least one further substance which is normally used in the processing sequence after application of the first substance.

The second portion of the device according to this embodiment can be connected to the first portion in any way, the aim being to ensure that when the substance is dispensed from the first chamber of the first portion, it cannot pass into the chamber of the second portion. Consequently, the chambers of the first portion cannot be connected to the chamber or chambers of the second portion via an openable passage area. For easier handling of the device, the second portion is preferably designed so that it can be detached from the first portion. A design of the connection piece which permits detachment by manual tearing is particularly expedient. This can be obtained, for example, by perforating the connection piece. However, any other design of the connection piece between the two portions is also conceivable and possible, for example by adhesive bonding with a further foil.

Since the substance located in the further chamber of the optionally present second portion is usually adapted to the nature of the substance in the other chamber, this reduces the risk of using substances which are not compatible with the first substance.

The device according to the invention is accordingly characterized in that substances or components, which cause storage problems, of a mixture which is to be produced are made ready within one package, in particular a disposable package, for dispensing and mixing. In particular, for example, three components can be stored separately in the device: in the first portion of the device, two components which are needed to prepare an adhesive mixture and, in the second portion, the third component in the form of a filling material which is adapted in terms of its chemical composition to the adhesive mixture.

Depending on the embodiment, the device is thus suitable not only for separate storage of several components, but also for mixing some of the components and for coordinated dispensing of the mixed components and of a further component which is adapted thereto and which in terms of its rheological properties is usually different than the two other components.

It is further ensured that all the substances stored in the device are filled on the same date, so that incompatibilities of the substances due to different expiry times can be excluded.

Thus, the device according to this embodiment is on the whole easy to handle since the first substance, which is located in the first chamber, can first be transferred into the pouch for removal, without complications and awkward opening of the device. After application of the substance from the pouch, a second substance is stored in the same device and made ready for application. The second substance, which usually differs in consistency from the first substance, is stored in a chamber which is to be opened in a different way than the first chamber.

The substance located in the first chamber can be dispensed by exerting pressure on the device, without removing a cover layer, whereas a cover sheet usually has to be torn off to remove the second substance from the chamber which is present in the second portion.

The device in this embodiment is thus distinguished by the fact that it has two portions with at least one chamber each for receiving in each case one substance, which substances are for their part to be removed from the device in different ways, and the individual chambers are opened in different ways.

The second portion of the device according to this embodiment usually likewise comprises two foils, usually a first foil in the form of a cover foil and a second foil in the form of a thermoformed foil. The first and second foils form a chamber for receiving a substance. The chamber can be opened in particular by means of the cover foil being pulled off. For this purpose, the first foil is preferably sealed onto the second foil in a peelable manner.

The device thus comprises two portions with chambers, which are each formed by two foils, the foils being connected or sealed to one another in different ways, depending on the embodiment.

The first and second foils can be multilayer foils. They have an optionally peelable outer layer area and an inner layer area.

The foils used are preferably those which have a sufficient diffusion density.

Depending on the nature of the substance to be stored, the foils should also be resistant to aggressive substances, for example, corrosive substances and/or substances which have solvent properties.

The foil components can be chosen from plastic foils, metal foils and ceramic foils.

Examples of suitable plastic foils are: PE, PP, PTFE, PET, PA, PBT, PVC, EVA, PVF (polyvinyl fluoride).

Examples of metal foils are: Al, Sn, Au, Ag, Fe.

Ceramic foils are to be understood as foils which have, for example, an SiOx-containing layer.

The foil can, in principle, have any desired structure and is adapted to the nature of the substances which are to be stored.

A foil structure has proven expedient which comprises in sequence, from outside to inside, PET, Al, PET, PE or PP, Al, PET, PE, if appropriate also without the PET foil as middle foil.

Adhesive additives can also be present between the foils.

Examples of adhesive additives are: laminating adhesives or extrusion lamination media.

The peelable outer layer area of the first foil which may be present is, preferably, opaque.

The inner layer area of the first foil is, preferably, transparent and, if appropriate, more flexible than the outer layer area.

The sequence, from outside to inside, of PET, Al or PP, Al has proven advantageous for the outer layer area.

The device comprises a container which has a first foil, for example, in the form of a cover foil, and a second foil, for example, in the form of a thermoformed foil, as is used in conventional blister packs.

Except for those areas forming the chambers, the foils are preferably connected flat to one another, preferably such that they are securely sealed to one another, except for the passage area that is to be selectively opened.

The first foil can be connected to the second foil, for example, by heat-sealing, cold-sealing, adhesive bonding or ultrasonic welding with sonotrodes.

The device can also be produced in a simple way depending on the embodiment. The areas which can be peeled open can be produced in one operation, in particular, by the action of the same energy application, even though these areas are situated on two different portions of the device.

A multilayer structure of the first foil and second foil can be obtained by laminating, calendering, coating of various single-foil layers, if appropriate also by vapor deposition, for example, with metals.

To ensure that the substances introduced into the device and to be applied are protected, for example, from incident light, the foils are preferably configured in such a way that, in an area surrounding the chamber, they are connected to one another by two spaced-apart sealing seams.

The receptacle or receptacles can be produced by the same methods as can be used to produce the device. The receptacle is, in this case, preferably produced by welding, adhesive bonding or sealing in the edge area of plastic-containing or metal-containing foils so that a cushion-shaped structure is preferably obtained. The foils are connected in such a way that the receptacle can be opened under the action of external pressure, the aim being that the receptacle should burst open in all directions under the effect of pressure.

The device can, in principle, be of any desired shape, but the shape is preferably adapted to the nature of the substances stored.

The chamber or chambers are preferably round (circular or oval), but, if appropriate, also angular (square, rectangular or triangular).

The chambers have volumes which are adapted to their purpose, so that if used correctly and with a plurality of components to be mixed together, they permit homogeneous mixing. The chamber adjacent to the pouch preferably has a volume which is suitable for receiving the total amount of substance which is to be mixed or has been mixed.

A chamber has, for example, a diameter of 5 to 20 mm, the dispensing instrument has a shaft diameter in the range of 2 to 4 mm. The substance volume which can be applied is usually in the range of a few tenths of a milliliter, preferably in the range of 0.03 to 0.5 ml. Depending on the embodiment, however, the substance volume which can be applied can also be a few milliliters, in particular 5 to 10 ml.

The volume of the receptacle is usually in the range of 0.01 to 8 ml, preferably in the range of 0.5 to 5 ml, particularly preferably in the range of 0.01 to 1.0 ml.

The pouch is open to one side and can be designed in such a way that it can also receive a dispensing instrument in the storage state. With a suitably small diameter of the pouch opening toward the outside, for example, in the form of a cannula, the pouch itself can also serve as an application device.

The separation between the chamber or chambers and the pouch is designed, in terms of distance and in terms of the strength of the adhesion, in such a way as to form a desired breaking point.

The passage area is configured in such a way that, in the storage state, it forms a tight closure both with respect to the pouch and also, if appropriate, with respect to the second chamber.

Such a desired breaking point can be obtained, for example, by cold-sealing, heat-sealing, ultrasonic welding or adhesive bonding. In the case of heat-sealing, a different energy application, preferably a lower energy application, is provided compared to the other sealed areas. This can be controlled by temperature, pressure and/or holding time.

Another possibility is to arrange, between the first and the second foils in the area of the desired breaking point, foreign particles which reduce the adhesion, for example peel foil punches or hot-melt adhesive spots. In this case, firmly sealing foils are preferably used as upper foil and lower foil.

The application instrument which is optionally present is preferably designed like a brush or a swab. An application instrument with a spherical tip bearing brush hairs or bristles has proven expedient. Pipets, cotton rods, sponges or spatulas can also be used as application instrument.

When using an application instrument, it is also expedient if the pouch is sealed off from the outside by the application instrument.

The device is preferably used for storing and dispensing substances, in particular, small amounts thereof, such as are used, for example, in the dental field.

The device is particularly suitable for storing aggressive and/or photosensitive substances.

To use the device, the optionally present outer layer area is first pulled off at least partially until it is possible to see the chambers containing the substances to be mixed, which substances can also be present in separate receptacles.

Moreover, the two foils in the region of the passage area that is to be selectively opened are designed to be separated from one another so that a connection can be established between the chamber and the pouch.

It is likewise necessary to open the optional receptacle or receptacles containing a substance.

This is preferably done by exerting external pressure on the chamber, for example, between the user's thumb and index finger. As a result, the receptacle or receptacles containing the substance burst open.

If the device has a first chamber and a second chamber which can be connected to one another via a passage area that is to be selectively opened, it is possible, by alternately pressing on the outer layer of the chambers containing the substances, to effect an alternating to and fro movement of the substances to be mixed through the selective opening created, before the mixed substances are transferred into the pouch adjacent to the chamber.

By kinking the device in the area between the chambers, the passage area or passage areas to be selectively opened can be closed again. It is then virtually impossible for the mixed substances to flow back into the other chamber, so that the mixed substances can be transferred into the pouch by exerting pressure on the outer area of the foils forming the chamber.

If the inner layer area of the first foil is transparent, it is possible to visually monitor the mixing procedure and the emptying from chamber to chamber or into the pouch.

A dispensing instrument which is present in the pouch, or which is introduced into it only at this time or at a later time, is wetted and can then be used to apply the released substance.

It is also conceivable for the dispensing instrument to be moved in the direction toward the chamber in order to free the passage area to be selectively opened and, if appropriate, to open the receptacle or receptacles located in the chamber. In this way too, the dispensing instrument is wetted.

If repeated application of the released substance is required, the dispensing instrument can be inserted back into the pouch.

The pouch or the dispensing instrument is preferably designed in such a way that, when the dispensing instrument is inserted back into the pouch, wetting of the outer area of the dispensing instrument does not take place.

This can be achieved, for example, by a channel-like configuration of the pouch and by adapting the configuration of the dispensing instrument to the latter.

It is also conceivable to provide a dish-shaped or cup-shaped configuration of the pouch end of the thermoformed foil into which the substance is conveyed for repeated wetting of the application instrument without wetting the shaft of the application instrument.

The present invention thus also relates to a method for using the device, which method comprises the following steps:

a) provision of a device as has been described above,
b) application of pressure to the first chamber of the first portion, by which means the receptacle located in this chamber opens,
c) mixing the first substance, emerging from the receptacle in step b), with a second substance which is located either in the first chamber outside the receptacle or in a second chamber which can be connected to the first chamber via a passage area that can be selectively opened,
d) transferring the mixture from step c) into the pouch via the passage area that can be selectively opened and wetting the application instrument which can be present in this pouch,
e) at least partial removal of the first substance from the pouch, if appropriate, with the aid of the application instrument,
f) if appropriate, application of the first substance onto a surface, in particular tissue, particularly preferably hard dental tissue,
g) if appropriate, opening the second chamber of the second portion by pulling off a cover foil,
h) if appropriate, at least partial removal of the second substance from the second chamber, and
i) if appropriate, application of the second substance onto the site which was previously wetted with the first substance or came into contact with the first substance.

Prior to activation of the device by opening one of the chambers or receptacles, the second portion is usually detached from the first portion of the device in order to facilitate the application of the substances which are located in the individual chambers.

The substances to be applied can be free-flowing, if appropriate, kneadable, or can also be present in powder form. The substances are preferably polymerizable.

Examples of polymerizable substances include photo-polymerizable or radical-polymerizable substances such as acrylic acid, methacrylic acid, maleic acid, both in monomer and polymer form or prepolymerized form, and derivatives thereof.

Free-flowing substances include all liquids and gels commonly used in the dental field, such as caustic agents, primers and bonding agents and customary solvents.

The solvents can be chosen from among both dipolar protic solvents and dipolar aprotic solvents. Examples which can be mentioned are: acetone, DMF, DMSO, alcohols, water.

All restorative and/or prosthetic substances common in the dental field, such as composites, compomers, ormocers, glass ionomer cements, silicate cements, phosphate cements, for example, in pastes or in powder form, can be introduced into the device.

The substances are located preferably in the receptacle or receptacles, if appropriate, in the receptacle or receptacles and at the same time in the chamber containing the receptacle or receptacles.

DETAILED DESCRIPTION OF THE DRAWINGS

The illustrative embodiments shown in the figures are given only as examples. The individual embodiments can be combined with one another at random.

Depending on the intended use, it can be advantageous if the device always has a further chamber for receiving a kneadable substance.

However, independently of the number of chambers and/or receptacles in the chambers, it is also conceivable for the device to always have an at least partially peelable outer layer area.

Figure 1:
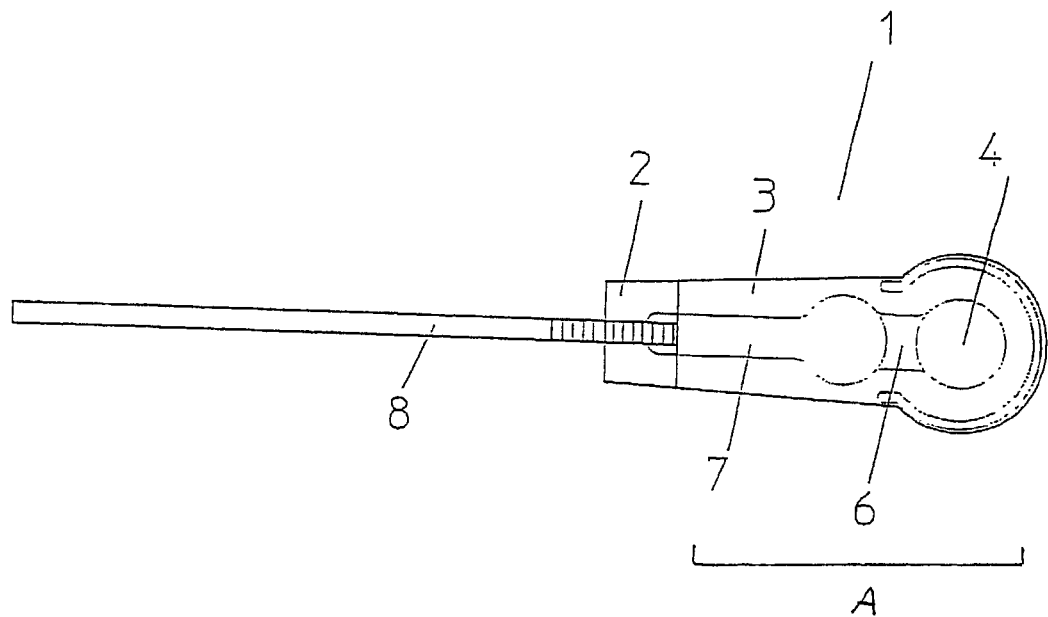
FIG. 1 shows a plan view of the device.

FIG. 1 shows the device (1) according to the invention in plan view, with a container which is formed by a first foil (2) and a second foil (3), a chamber (4), a passage area (6) that can be selectively opened, and a pouch (7) in which a dispensing instrument (8) is located.

Figure 2:
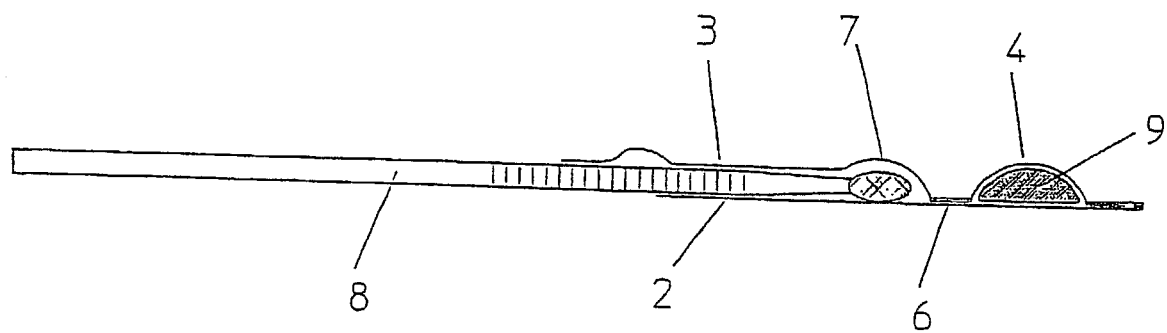
FIG. 2 shows a longitudinal section through the device with a chamber which comprises a receptacle.

FIG. 2 shows the device according to the invention in longitudinal section, with a receptacle (9) which is provided in the chamber and which can contain a substance. In addition to the receptacle (9) containing a first substance, the chamber can also contain a further substance which surrounds the receptacle.

Figure 3:
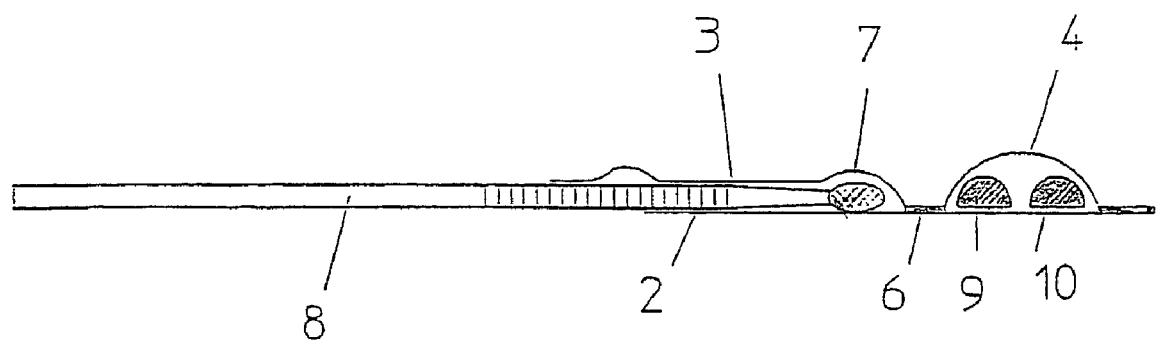
FIG. 3 shows a longitudinal section through the device with a chamber which comprises two receptacles.

In the device shown in longitudinal section in FIG. 3, the chamber (4) contains two receptacles (9, 10) which can contain substances. In addition to the receptacles (9, 10) containing a first substance and a second substance, the chamber can also contain a further, third substance which surrounds the receptacles.

Figure 4:
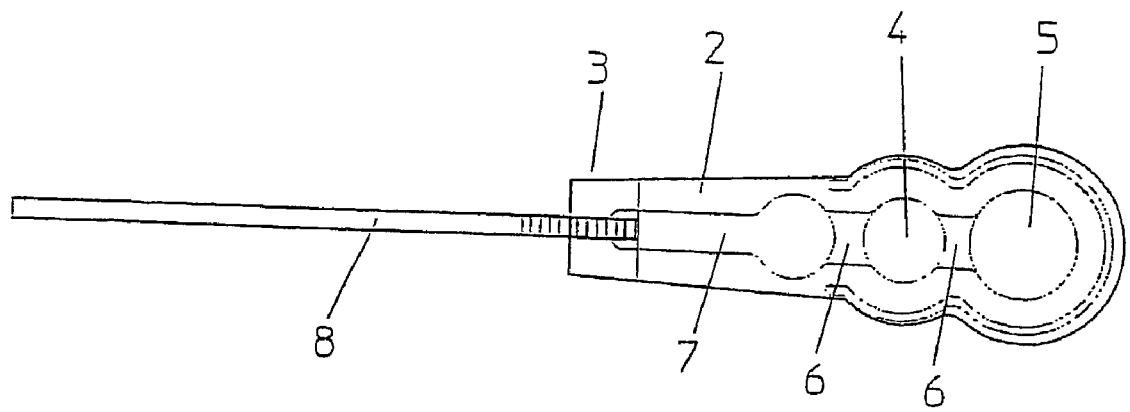
FIG. 4 shows a plan view of the device with two chambers.

FIG. 4 shows the device as in FIG. 1 with two chambers (4, 5) in plan view, the chambers (4, 5) being connected to one another via a passage area (6) that can be selectively opened.

Figure 5:
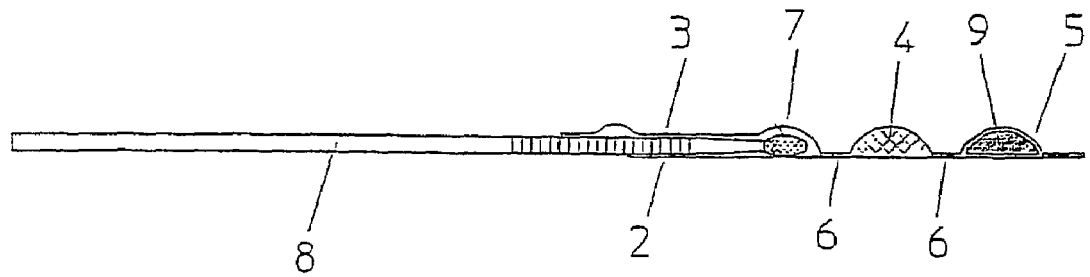
FIG. 5 shows a longitudinal section through the device with two chambers and one receptacle.

In the embodiment shown in FIG. 5, the device has two chambers (4, 5), said chambers being connected to one another via a passage area (6) that can be selectively opened, and one of the chambers containing a receptacle (9).

Figure 6:
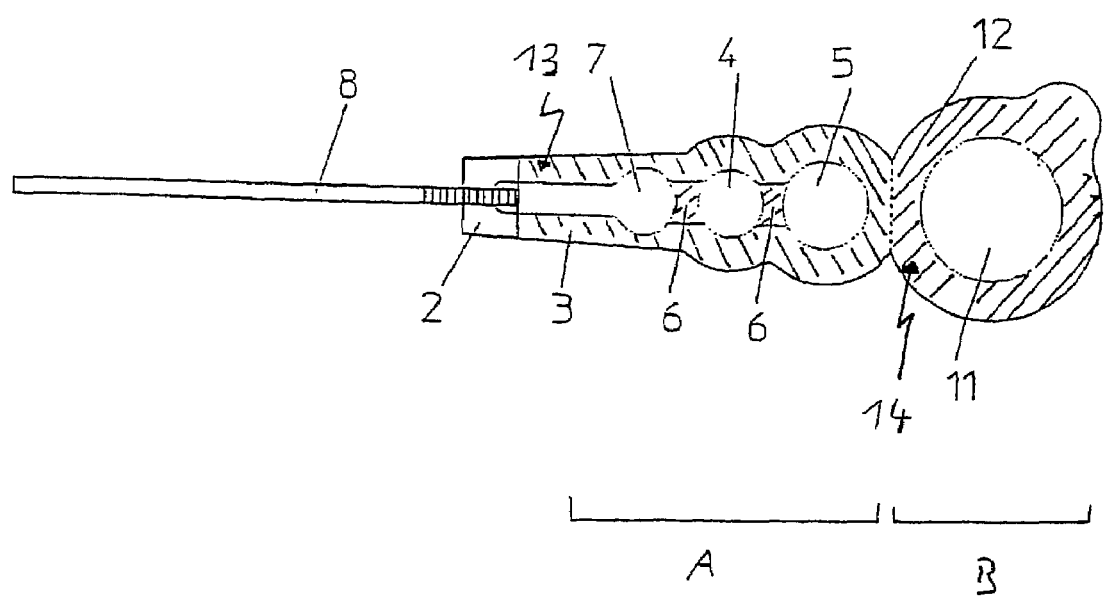
FIG. 6 shows a plan view of the device with three chambers which are arranged on two portions.

FIG. 6 shows an embodiment with two chambers (4, 5) which are arranged on a first portion (A) and which are connected to one another via a passage area (6) that can be selectively opened, and with a separate chamber (11) which is arranged on a portion (B), the chamber (11) not being connected to the other chambers via an area that can be opened. In the embodiment shown, the separate chamber (11) is designed so that it can be detached from the rest of the device via a perforation (12). The perforation (12) on the one hand permits, if appropriate, the complete detachment of the further chamber (11), while on the other hand it is intended to ensure that, when the further chamber (11) is opened by pulling off the cover foil, the entire outer foil is not pulled off. The foils forming the chambers are connected to one another in different ways in the areas (13, 14). Whereas the foils in the first area (14) are sealed securely together (hatched lines from left to right), they are sealed to one another in such a way that they are peelable in the second area (13) (hatched lines from right to left).

Figure 7:
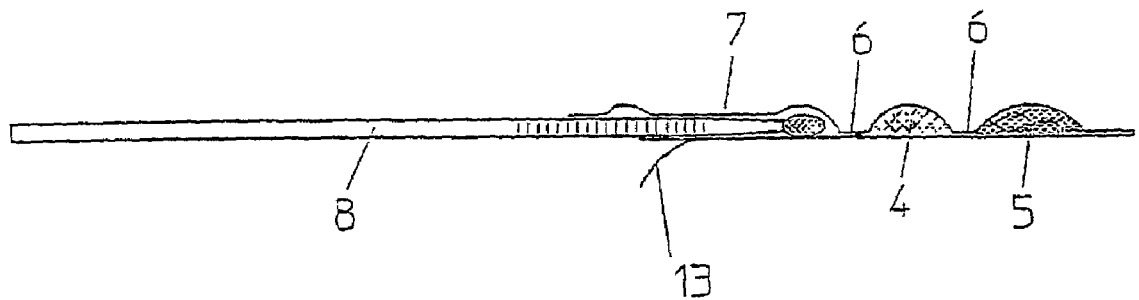
FIG. 7 shows a longitudinal section through the device with two chambers, where a foil has a peelable outer layer area.

In FIG. 7, an embodiment of the device is shown in longitudinal section with two chambers (4, 5), where one of the foils forming the device comprises a peelable outer layer area (13).

The invention claimed is:

1. A device, comprising:
a first chamber formed by a first foil and a second foil;
a closed first receptacle in said first chamber;
a pouch; and
a first selectively-openable passage area disposed between said first chamber and said pouch, wherein
said receptacle is openable by applying pressure to said first foil and said second foil such that when opened, a first substance in said first receptacle becomes available to pass through said first chamber and said passage area into said pouch.

2. A device according to claim 1, further comprising a second chamber for receiving a second substance.

3. A device according to claim 2, further comprising:
a second selectively-openable passage area disposed between said second chamber and said first chamber;
wherein said second passage area is selectively openable.

4. A device according to claim 2, further comprising at least one receptacle in said second chamber.

5. A device according to claim 2, further comprising a second portion having a second portion chamber,
wherein said second portion chamber receives a second portion substance; and
wherein said first chamber, said pouch, and said second chamber comprise a first portion of the device.

6. A device according to claim 5, further comprising a separating region between said second portion chamber and said chambers of said first portion, wherein said separating region is not selectively openable.

7. A device according to claim 5, wherein said second portion chamber further comprises a separately peelable foil.

8. A device according to claim 7, wherein said separately peelable foil is resealable.

9. A device according to claim 1, further comprising additional receptacles in said first chamber.

10. A device according to claim 1, wherein said pouch is designed to receive a dispensing instrument.

11. A device according to claim 1, further comprising a dispensing instrument, wherein said dispensing instrument is received in said pouch and a section of said dispensing instrument protrudes from said pouch.

12. A device according to claim 1, wherein one of said first foil or said second foil comprises a peelable outer layer area and an inner layer area.

13. A device according to claim 1, further comprising a second portion having a second portion chamber,
wherein said second portion chamber receives a second portion substance; and
wherein said first chamber and said pouch comprise a first portion of the device.

14. A device according to claim 13, further comprising a separating region between said second portion chamber and said first chamber of said first portion, wherein said separating region is not selectively openable.

15. A device according to claim 13, wherein said second portion chamber further comprises a separately peelable foil.

16. A device according to claim 15, wherein said separately peelable foil is resealable.

17. A device according to claim 1, further comprising a substance in said receptacle.

18. A device according to claim 1, further comprising a substance in said first chamber.

19. A method of using a device, comprising:
storing at least one free-flowing substance in a device according to claim 1; and
dispensing said at least one free-flowing substance.

20. A method of using a device according to claim 19, further comprising:
storing a kneadable substance in the device; and
dispensing said kneadable substance from the device.

21. A method of dispensing a mixture from a device, the device comprising:
a first chamber formed by a first foil and a second foil;
a closed receptacle containing a first substance in said first chamber and openable by applying pressure to said first foil and said second foil;
a pouch;
a second substance provided in said first chamber or in a second chamber; and
a selectively-openable passage area between said first chamber and said pouch,
said method comprising:
applying pressure to said first foil and said second foil to open said receptacle;
mixing said first substance from said receptacle with said second substance to form a mixture;
transferring said mixture to said pouch via said selectively-openable passageway; and removing at least a portion of said material from said pouch, wherein said second chamber, when present, is connected to said first chamber via a selectively-openable passage area.

22. A method according to claim 21, wherein said mixture is an agent for treating a tooth surface.

23. A method of making a storing and dispensing device, comprising:

forming a first chamber with a first foil and a second foil;

providing a closed receptacle in said first chamber;

providing a pouch;

creating a selectively-openable passage area between said first chamber and said pouch; and providing at least one substance in the device, wherein said receptacle is openable by applying pressure to said first foil and said second foil.

24. A method of making a device according to claim 23, wherein said at least one substance is a component of an agent for treating a tooth surface.

* * * * *